United States Patent [19]
Phelps et al.

[11] 4,383,908
[45] May 17, 1983

[54] PROBE SYSTEM FOR DETERMINING ACIDITY OF FLUID FLOWING THROUGH PRESSURIZED PIPE LINE

[75] Inventors: Thomas C. Phelps, Gaston; Clifford J. Reese, Ronoke Rapids, both of N.C.

[73] Assignee: Champion International Corporation, Stamford, Conn.

[21] Appl. No.: 304,344

[22] Filed: Sep. 22, 1981

Related U.S. Application Data

[63] Continuation of Ser. No. 135,301, Mar. 31, 1980, abandoned, which is a continuation of Ser. No. 31,392, Apr. 19, 1979, Pat. No. 4,202,749.

[51] Int. Cl.³ .............................................. G01N 27/36
[52] U.S. Cl. .................................... 204/409; 324/438; 204/433
[58] Field of Search .................. 204/1 H, 1 T, 195 G, 204/195 R; 324/438

[56] References Cited

U.S. PATENT DOCUMENTS

| | | | |
|---|---|---|---|
| 1,683,489 | 9/1928 | Rice | 73/86 |
| 2,986,511 | 5/1961 | Digby | 204/195 G |
| 3,398,079 | 8/1968 | Arthur et al. | 204/195 G |
| 3,434,953 | 3/1969 | Porter et al. | 204/195 G |
| 3,471,393 | 10/1969 | Ingruber | 204/195 R |
| 3,718,034 | 2/1973 | Swearingen | 73/86 |
| 3,980,542 | 9/1976 | Winslow et al. | 73/86 |
| 4,002,059 | 1/1977 | Jeffers et al. | 73/86 |
| 4,008,141 | 2/1977 | Kotani et al. | 204/195 G |
| 4,016,063 | 4/1977 | Radnoti | 204/195 G |
| 4,128,468 | 12/1978 | Bukamier | 204/195 G |

FOREIGN PATENT DOCUMENTS

| | | | |
|---|---|---|---|
| 1237808 | 3/1967 | Fed. Rep. of Germany | 204/195 G |

Primary Examiner—G. L. Kaplan
Attorney, Agent, or Firm—Evelyn M. Sommer

[57] ABSTRACT

A probe system is provided which may be removably installed in-line in a pressurized pipe line to determine the pH of the fluid flowing therethrough. The probe system comprises a mounting means exteriorly secured to the pipe line, a valve means in said mounting means and a cap means secured to the mounting means and having an opening therein. An elongated pH probe is inserted through said opening and is secured by said mounting means while the probe tip is disposed within the pipe line. The probe includes a transducer for converting the acidity of the fluid flowing through the pipe line to an electrical signal representing the acidity, and a smooth, adherent plastic coating is provided on said probe to define an elongated sheath with a uniform, round circumference. A sealing means seals against the sheath to prevent fluid flow past the cap means, said sealing means permitting movement of the sheath relative to said cap means upon installation and removal of the probe within the pipe line.

3 Claims, 3 Drawing Figures

PROBE SYSTEM FOR DETERMINING ACIDITY OF FLUID FLOWING THROUGH PRESSURIZED PIPE LINE

This is a continuation of application Ser. No. 135,301, filed Mar. 31, 1980, now abandoned, which, in turn, is a continuation of Serial No. 31,392, filed Apr. 19, 1979 and now U.S. Pat. No. 4,202,749.

BACKGROUND OF THE INVENTION

The present invention relates to instruments used for measuring acidity or alkalinity and is particularly related to a pH probe system which may be removably installed in a pressurized pipe line to measure the pH of fluid flowing therethrough.

The term "pH" is well known in the art, and it is a measure of acidity or alkalinity of a product. Thus a pH of 7 indicates that the product is neutral; a pH of less than 7 indicates that it is acidic while a pH greater than 7 indicates that it is alkaline.

It is also known that pH probes have heretofore been widely used to measure the acidity of liquids. A pH probe is a transducer which converts the pH measurement into an electrical signal which has a predetermined relationship to the pH.

It is additionally a common knowledge to those familiar with the paper industry that the pH of the raw stock in a paper mill may be measured by a batch type of raw stock pH monitoring system. However, there have been two basic problems with such pH systems.

First, it has been found in actual paper mill conditions that a continuous sample flow could not be maintained to the sample chamber within which the pH probe is disposed. If the consistency of the raw stock was 3.5% or over, the raw stock would be so thick that it would choke the sample line. It has been suggested that the flow of thick viscous liquid raw stock could be improved by increasing the diameter of the same line to try to prevent choke-ups. While increase in the size of the sample line did lessen the choke-up problem, in practice it caused another problem. The line from the sample chamber would sometimes choke-up, due to the thick raw stock, and the raw stock would overflow from the sample chamber to the floor.

Secondly, when an acid was introduced into the raw stock chest, it was found that the agitation in the chest was insufficient, due to the thickness of the material, its consistency being above 3.5%. This caused pockets of acid to form in the raw stock chest, resulting in a big cycle in pH (a fast rise acidity indication when on automatic control). The only way the system could be run was by taking manual samples, a slow and costly procedure. There is also the problem of insufficient agitation because the stock may be from 4% to 5% consistency.

It has been suggested that the batch system could be returned to service by running new sample lines, building and installing new stainless steel sample chambers and running the overflow lines back to the raw stock chest. This, however, is expensive and no more effective than the original system.

A commercially available pH probe system is known which could function under pressure, namely, the Horiba Industrial pH (Model K7) which operates under one hundred pounds per square inch pressure (hereinafter called the "Horiba Model K7"). However, the Horiba Model K7 is not intended or adapted to fit in a pressurized pipe line since it is designed as an open-tank type probe.

U.S. Pat. No. 4,008,141 to Horiba, manufacturers of the Model K7, describes a pH probe which utilizes a replaceable glass electrode and a reference electrode. The glass electrode includes a glass membrane containing an electrode within a saturated aqueous solution of potassium chloride. The reference electrode is within a space filled with the same type of solution and has a porous wall.

There are other patents which describe various types of pH probes. Thus, U.S. Pat. No. 4,016,063 entitled "Electrode Shield", shows a glass shield to protect the "fragile glass electrodes" used in pH measurements, wherein the shield is removable from the probe.

U.S. Pat. No. 3,980,542, entitled "Flush Mounted Probe For Corrosion Testing", shows a mounting structure welded to a pipe line to detect the thin liquid film on the interior pipe line wall. The probe described in this patent uses exposed electrodes.

In U.S. Pat. No. 3,471,393, entitled "Apparatus For Testing Liquids Utilizing A Plurality Of Probes Or Electrodes With Sensitive Ends Converging In Liquid Flow Path", the probes are mounted on an instrument casing which has inlet and outlet pipes. This patent describes a pH probe whose glass electrode, reference electrode and temperature sensitive probe are immersed in a chamber formed by the instrument casing.

None of the pH probe systems which have heretofore been available have been entirely satisfactory for in-line installation in conjunction with pressurized pipe lines.

Accordingly, it is an object of the present invention to provide a pH probe system that can be used "in-line" with a pressurized pipe line.

It is a further object of the present invention to provide a pH probe system that can be used to measure the acidity of thick raw stock in a paper mill even when the raw stock is over 3.5% concentration.

It is still a further object of the present invention to provide a pH probe system that can be installed and removed from the pressurized pipe line without spillage of fluid.

It is still a further object of the present invention to provide a mounting means for securing the probe to the pipe line so that it is not moved or injured by the flow of fluid within the pipe line.

It is yet another object of the present invention to provide a pH probe system which may be fabricated from relatively low-cost and commercially available parts in order to manufacture and install the probe system at relatively low costs.

The foregoing and other features of the invention will be more clearly comprehended from the ensuing detailed description of the invention taken in conjunction with the drawings.

SUMMARY OF THE INVENTION

In accordance with the present invention, a pH probe system is provided which is uniquely suitable for installation in a pressurized, fluid-carrying pipe line. The pH probe system of this invention may be used to measure the acidity of raw stock in a paper mill even when the concentration of the raw stock is in excess of 3.5%.

The probe system comprises a mounting means, including a valve means (such as a gate valve), exteriorly secured to the pipe line. The mounting means has a cap means removably secured thereto, said cap means having an opening through which an elongated pH probe may be inserted so that its pH sensor tip is disposed within the pipe line.

The pH probe includes a transducer for converting the pH of the fluid flowing through the pipe line to an electrical signal which represents the acidity of the fluid. The probe is coated with a smooth, adherent plastic coating to form an elongated sheath having a uniform exterior shape and size along its length. Sealing means such as an "O" ring is positioned within the cap means to seal against the sheath and prevent fluid from flowing past the cap means. The sealing means permits movement of the sheath relative to the cap means during installation and removal of the probe.

BRIEF DESCRIPTION OF THE DRAWINGS

In the drawings, wherein like numerals are employed to designate like parts.

DETAILED DESCRIPTION OF THE INVENTION

Figure 1:
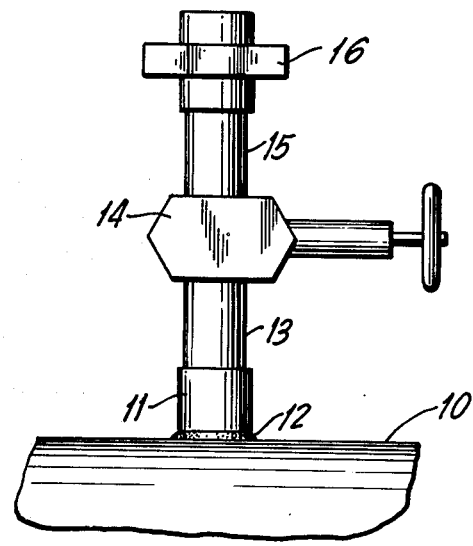
FIG. 1 is a side plan view of the mounting means of the pH probe system of this invention.

Referring to FIG. 1, the mounting means employed with the pH probe of the present invention includes a pipe coupling 11 suitably welded to a pipe line 10 such as by a ring of welding material 12. The pipe line 10 is conveniently a metal raw stock pipe through which flows a pressurized acidic raw stock such as that encountered in a paper mill. However, the probe system may also be used in conjunction with other types of pipe lines.

The pipe coupling 11 is interiorly threaded to threadedly engage with a an exteriorly threaded pipe nipple 13, and a gate valve 14 is securely mounted between the pipe nipple 13 and a second pipe nipple 15 as shown in FIG. 1. An interiorly threaded pipe union 16 is secured to the second pipe nipple 15 and is used for connection to the probe system shown in FIG. 2 as hereinafter described.

Figure 2:
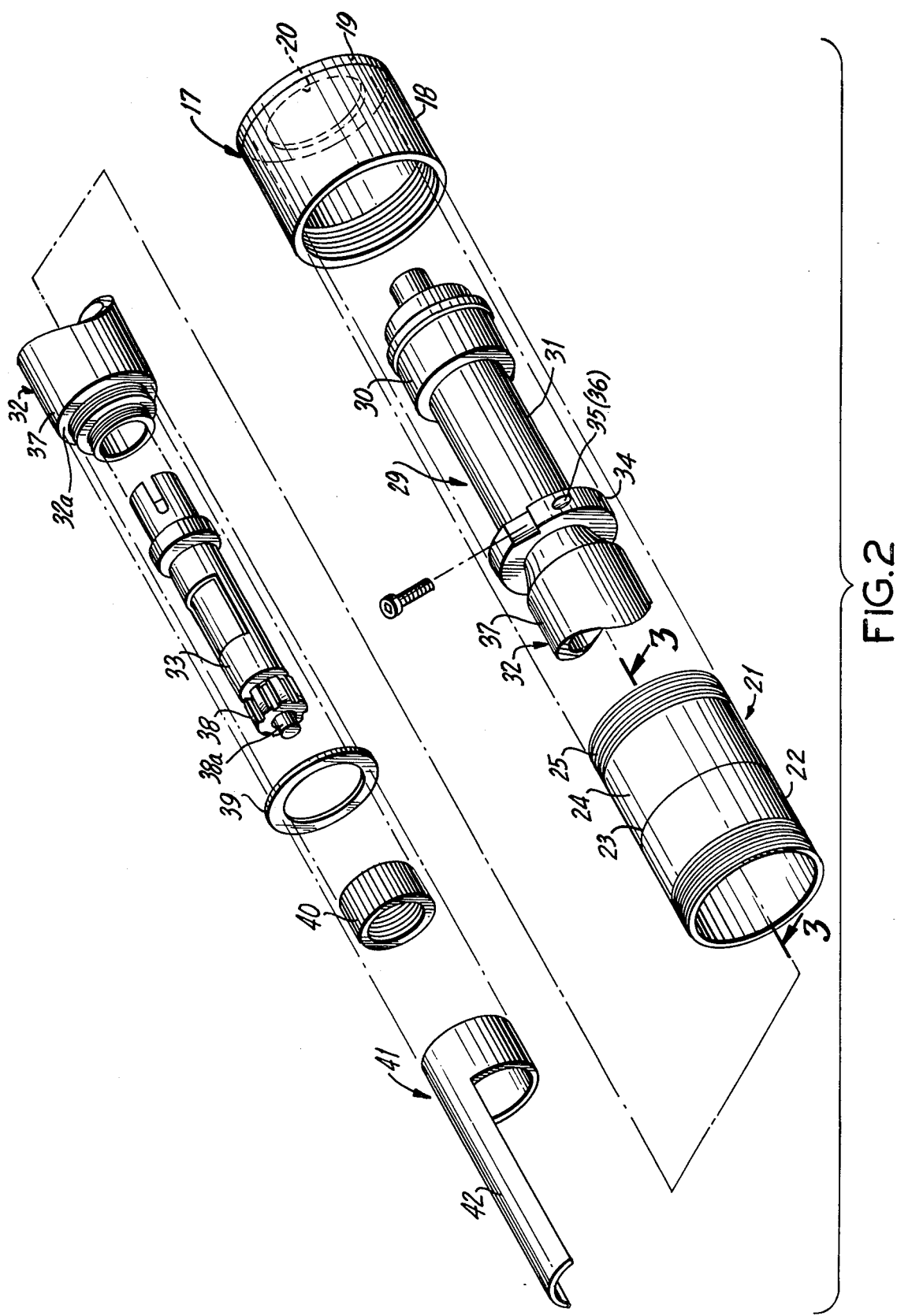
FIG. 2 is an exploded perspective view of the pH probe of the present invention.

Referring now to FIG. 2, the probe system 17 includes a unitary pipe coupling 18 welded to a washer 19 to define a reduced orifice 20. The pipe coupling 18 is threadedly engaged onto a unitary "O" ring sleeve and pipe nipple unit 21.

Figure 3:
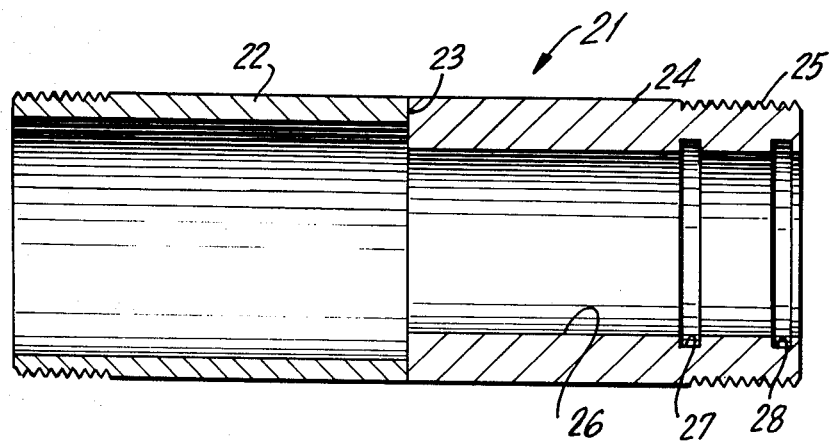
FIG. 3 is a cross-sectional view taken along the line 3—3 of FIG. 2.

As shown in FIG. 3, the "O" ring sleeve and pipe nipple unit 21 consists of a pipe nipple 22 and "O" ring sleeve 24, wherein the pipe nipple 22 is exteriorly threaded for threaded engagement with the interiorly threaded pipe union 16. The pipe nipple 22 is welded to the "O" ring sleeve 24 as shown at 23 and the "O" ring sleeve 24 is exteriorly threaded as shown at 25. The interior circumferential wall 26 of the "O" ring sleeve 24 has a pair of circumferential grooves 27, 28 and a flexible "O" ring is positioned in each of said grooves.

Referring once again to FIG. 2, the probe 29 comprises an upper cylindrical body portion 30, a cylindrical reduced body portion 31, an intermediate elongated body portion 32 and a sensor head portion 33. A split retaining ring 34 is secured on the reduced body portion 31 and has a pair of opposite holes 35, 36 (hole 36 not being visible in FIG. 2) tapped therein for receiving tap screws to hold the two parts of the split ring together so as to form a unitary ring. The outer diameter of a retaining ring 34 is less than the inside diameter of the unitary pipe coupling 18 but is larger than the inside diameter of the "O" ring sleeve 24 so that the ring may fit and be held between "O" ring sleeve 24 and unitary pipe coupling 18.

The elongated body portion 32 is coated with an adherent coating 37 which is, preferably, woven filaments of glass, such as "Fiberglass"® impregnated with a plastic resin such as, for example, a polyester resin, and a hardener. After the plastic coating has dried and set, it is machined to form a smooth outer surface. Thus, the elongated body portion 32 with its exterior smooth plastic surface slides within the aforementioned "O" rings and "O" ring sleeve during installation and removal of the probe. The upper end of the plastic-coated elongated body portion 32 is tapered so it can readily slide into the "O" rings which are secured in the grooves 27, 28.

The sensor head portion of the probe includes the glass electrode pH (ORP) tip 38A, and its retaining "G nut" 38. The retaining washer 39 slides over the "G nut" 38, tip 38A, and rests on elongated body portion 32, at its upper shoulder. It is held captive there when protector shield 41 is attached by threading on at upper threads 32A. The protector shield 41 fits over the sensor head portion of the probe and has a flange 42 positioned in the direction of the flow of fluid in order to protect the sensor portion of the probe. The protector shield flange 42 should be cut to extend the same distance as the pH (ORP) tip, but not to extend beyond the tip.

The retaining washer 39 is used to limit the withdrawal of elongated body portion 32, and prevent blow out of unit until hand valve 14 can be closed. Pipe union 16 can than be separated for complete removal of probe assembly 25 from pipe line 10.

The "G nut" 38, has extended flanges on bottom end, at tip 38A, to protect the tip. These flanges were cut off to prevent a build up of stock on probe tip.

It will be understood that various pH probes may be used in connection with the probe system of the present invention. However, the probe system of the present invention is particularly adapted for use, in its preferred embodiment, with the model K7 probe of Horiba Industrial Corporation of Kyoto, Japan. That probe has two electrodes which may be electrically connected to a series of electrical instruments available from the same Horiba Company, the series of instruments being a converter, an indicator and a power supply. The power supply produces a current in the 4–20 milliamp range which is transmitted to suitable recording or control devices, or both. For example, the signal may be transmitted to a pH recorder and to a pH controller which automatically controls a valve to admit liquid chemicals, such as acid, into the pipe line, in accordance with a predetermined program or standard.

What is claimed is:

1. A pH probe system having a pH probe adapted to be removably installed in-line within a pressurized pipe line to determine the pH of a fluid flowing through the pipe line, said system comprising:
    (a) a pipe assembly mounted on the pipe line for providing access to the interior of the pipe line;
    (b) valve means for closing and opening said pipe assembly, said valve means being disposed medially of said pipe assembly;
    (c) a sleeve mounted on an outer end of said pipe assembly, said sleeve having a bore opening into said pipe assembly;

(d) a pH probe assembly telescopingly mounted in said sleeve, said probe assembly extending through said sleeve bore and through said pipe assembly, said probe assembly being operable to convert the pH of the fluid flowing through the pipe line to an electrical signal representing the acidity of the fluid, and said probe assembly having a sensor head portion and a glass electrode disposed at an inner end of said sensor head portion within said pipe line;

(e) sealing means providing a fluid-tight seal between said probe assembly and said sleeve bore; and (f) a protector shield secured to said probe assembly, said protector shield including an elongated flange disposed outwardly spaced from and adjacent to said sensor head portion on the upstream side of said sensor head portion within said pipe line, said protector shield being operative to protect said sensor head portion and said electrode from dynamic fluid flow forces within said pipe line on the upstream side while allowing exposure of said sensor head portion and said electrode to the fluid in said pipe line on the downstream side.

2. The pH probe system of claim 1, further comprising a retaining washer secured to said probe assembly adjacent to said sensor head portion, said retaining washer being held in place by engagement with said protector shield, and said retaining washer being operative to prevent the fluid in said pipe line from entering said sleeve when said probe assembly is withdrawn from said sleeve prior to closing said valve means.

3. The pH probe system of claim 1, wherein said protector shield flange extends for substantially the same distance on said probe system as said glass electrode.

* * * * *